(12) United States Patent
Crump et al.

(10) Patent No.: US 9,324,129 B2
(45) Date of Patent: Apr. 26, 2016

(54) METHOD AND APPARATUS FOR SINGLE-AXIS CROSS-SECTIONAL SCANNING OF PARTS

(76) Inventors: Craig D. Crump, Eden Prairie, MN (US); Brad Kahler, Bloomington, MN (US); Dan Braegelman, Plymouth, MN (US)

( * ) Notice: Subject to any disclaimer, the term of this patent is extended or adjusted under 35 U.S.C. 154(b) by 242 days.

(21) Appl. No.: 12/993,525

(22) PCT Filed: May 15, 2009

(86) PCT No.: PCT/US2009/044095
§ 371 (c)(1),
(2), (4) Date: Nov. 19, 2010

(87) PCT Pub. No.: WO2009/143005
PCT Pub. Date: Nov. 26, 2009

(65) Prior Publication Data
US 2011/0069300 A1    Mar. 24, 2011

Related U.S. Application Data

(60) Provisional application No. 61/054,256, filed on May 19, 2008.

(51) Int. Cl.
*G01N 1/28* (2006.01)
*G06T 3/00* (2006.01)
(Continued)

(52) U.S. Cl.
CPC ... *G06T 3/00* (2013.01); *G01N 1/286* (2013.01); *G06T 17/10* (2013.01); *G01N 2001/061* (2013.01); *G01N 2001/366* (2013.01)

(58) Field of Classification Search
CPC .............. G06T 3/00; G01N 1/28; G01N 1/04; G01N 2001/061
USPC ........................................... 356/36, 601–613
See application file for complete search history.

(56) References Cited

U.S. PATENT DOCUMENTS 2,328,494 A * 8/1943 Reaney .......................... 407/34
2,584,738 A * 2/1952 Reitz ............................. 144/115
(Continued)

FOREIGN PATENT DOCUMENTS

EP    1 890 137 A1    5/2007
JP    2000-190278 A   7/2000

OTHER PUBLICATIONS

The State Intellectual Property Office of the People's Republic of China, "Notice on the First Office Action" for Application No. 200980118442.3, Applicant The Crump Group, Inc., China, May 4, 2012.
(Continued)

*Primary Examiner* — Kara E Geisel
*Assistant Examiner* — Dominic J Bologna
(74) *Attorney, Agent, or Firm* — Patterson Thuente Pedersen, P.A.

(57) ABSTRACT

Improved methods and apparatus for cross-sectional scanning of parts employ a scanning station in which the focal plane of the scanning apparatus never moves in the vertical direction, i.e., the direction in which the stage of the part/potting combination moves. Distinct steps of material removal and scanning alternate with an intermediate step of moving the part/potting combination in the vertical direction after a surface layer has been removed, thus placing the newly-created surface back into the non-moving focal plane for the next scanning step. A removal station (not the stage carrying the part/potting combination) repeatedly moves into and out of the field of view of the scanning station between scanning steps. The material removal station is specially configured to remove the desired surface layer of the part/potting combination and the created debris, without requiring the separate environment characteristic of previous commercial applications.

53 Claims, 2 Drawing Sheets

(51) Int. Cl.
*G06T 17/10* (2006.01)
*G01N 1/06* (2006.01)
*G01N 1/36* (2006.01)

(56) References Cited

U.S. PATENT DOCUMENTS

| | | | |
|---|---|---|---|
| 3,649,108 A | | 3/1972 | Ahrens |
| 3,650,178 A | * | 3/1972 | Appleton ............... 409/202 |
| 3,800,650 A | | 4/1974 | Schroder |
| 3,817,647 A | | 6/1974 | Lemelson |
| 3,855,889 A | | 12/1974 | Wiley et al. |
| 3,884,563 A | | 5/1975 | Evans et al. |
| 4,168,897 A | | 9/1979 | Gates |
| 4,272,049 A | | 6/1981 | Kindel |
| 4,309,600 A | | 1/1982 | Perry et al. |
| 4,369,563 A | | 1/1983 | Williamson |
| 4,404,684 A | | 9/1983 | Takada |
| 4,721,952 A | | 1/1988 | Huber |
| 4,879,659 A | | 11/1989 | Bowlin et al. |
| 4,912,644 A | | 3/1990 | Aoyama et al. |
| 4,928,313 A | | 5/1990 | Leonard et al. |
| 4,960,330 A | | 10/1990 | Kerschmann |
| 4,975,972 A | | 12/1990 | Bose et al. |
| 4,977,512 A | | 12/1990 | Nakagawa |
| 5,019,993 A | | 5/1991 | Montalcini et al. |
| 5,040,007 A | | 8/1991 | Haguida |
| 5,107,444 A | | 4/1992 | Wu |
| 5,113,490 A | | 5/1992 | Winget |
| 5,139,338 A | * | 8/1992 | Pomerantz et al. ............ 356/601 |
| 5,172,326 A | | 12/1992 | Campbell, Jr. et al. |
| 5,239,591 A | | 8/1993 | Ranganath |
| 5,276,783 A | | 1/1994 | Fossum |
| 5,309,366 A | | 5/1994 | Grenkowitz |
| 5,323,327 A | | 6/1994 | Carmichael et al. |
| 5,377,011 A | | 12/1994 | Koch |
| 5,432,704 A | * | 7/1995 | Vouzelaud et al. ............ 700/182 |
| 5,519,816 A | * | 5/1996 | Pomerantz et al. ............ 345/419 |
| 5,538,372 A | * | 7/1996 | Cuneo et al. ............... 409/131 |
| 5,621,648 A | | 4/1997 | Crump |
| 5,703,782 A | * | 12/1997 | Dundorf ............... 700/182 |
| 5,710,645 A | | 1/1998 | Phillips et al. |
| 5,880,961 A | * | 3/1999 | Crump ............... 700/112 |
| 5,988,862 A | | 11/1999 | Kacyra et al. |
| 6,059,494 A | * | 5/2000 | Susnjara ............... 409/134 |
| 6,079,078 A | * | 6/2000 | Byington ............... 15/339 |
| 6,091,999 A | | 7/2000 | Crump et al. |
| 6,209,429 B1 | * | 4/2001 | Urso et al. ............... 82/1.11 |
| 6,407,735 B2 | | 6/2002 | Kressin |
| 6,718,854 B2 | * | 4/2004 | Bedi et al. ............... 82/118 |
| 2002/0129485 A1 | * | 9/2002 | Mok et al. ............... 29/527.2 |
| 2004/0258495 A1 | * | 12/2004 | Kakino et al. ............... 409/132 |
| 2006/0072123 A1 | | 4/2006 | Wilson et al. |
| 2008/0109986 A1 | * | 5/2008 | Loveless ............... 15/401 |

OTHER PUBLICATIONS

Intellectual Property Office of Singapore, "Search and Examination Report" for Application No. 20108316-0, Applicant The Crump Group, Inc., Singapore, Jun. 6, 2012.

Crump, "3-D, Non-Contact Scanning for Inspection," Moldmaking Technology, Mar. 2007 (reprint), Gardner Publications, Inc., Cincinnati, Ohio.

Little et al.., "The Industrial Computed Tomography cell", *The Leading Edge*, Winter 1989/1990 pp. 10-15.

Wohlers, "Reverse Engineering Systems," *Cadence*, Jan. 1993, pp. 45-57.

Yancey et al., "Reverse Engineering Using Computed Tomography", presented at the Conference on Rapid Prototyping, Dayton, OH, Jun. 1994, pp. 1-9.

Ioannides et al., "Reverse Engineering, Rapid Prototyping: Generation of Surface Information by Using a 4D-Laser Scanner for Digitization", University of Stuttgart, Feb. 1994, pp. 389-393.

Roth-Koch, Sabine et al., "Efficiently Digitizing of Free Formed Moulds and Tools with 3D-Laserscanning," Fraunhofer-Institute for Mfg. Engineering and Automation, Feb. 1994, pp. 363-371.

United States Patent and Trademark Office, Prosecution documents from U.S. Appl. No. 11/939,754, filed Nov. 14, 2007, Applicant Craig D. Crump, Assignee The Crump Group, Inc.

United States Patent and Trademark Office, Prosecution documents from U.S. Appl. No. 08/284,253, filed Aug. 2, 1994, Applicant Craig D. Crump, Assignee The Crump Group, Inc.

United States Patent and Trademark Office, Prosecution documents from U.S. Appl. No. 08/638,915, filed Apr. 25, 1996, Applicant Craig D. Crump, Assignee The Crump Group, Inc.

United States Patent and Trademark Office, Prosecution documents from U.S. Appl. No. 08/970,172, filed Nov. 13, 1997, Applicant Kenneth R. Kressin, Assignee The Crump Group, Inc.

United States Patent and Trademark Office, Prosecution documents from U.S. Appl. No. 09/152,218, filed Sep. 11, 1998, Applicant Craig D. Crump et al., Assignee The Crump Group, Inc.

CGI, *CSS Software Manual for the CSS-1000*, Sep. 2001, Version 2.07, 51 pages.

CGI, *CSS Pre-Installation Packet CSS-1000-new*, Nov. 13, 2010, 14 pages.

CGI, *CSS-300 Inspection System Pre-Install Setup*, Oct. 22, 2013, 13 pages.

* cited by examiner

METHOD AND APPARATUS FOR SINGLE-AXIS CROSS-SECTIONAL SCANNING OF PARTS

RELATED APPLICATIONS

The present application is a National Phase entry of PCT Application No. PCT/US2009/044095, filed May 15, 2009, which claims the benefit of U.S. Application No. 61/054,256, filed May 19, 2008, each of which is incorporated herein by reference in its entirety.

BACKGROUND

Cross-sectional scanning of parts, and the processing of the data generated in the same, is described in U.S. Pat. Nos. 5,139,338; 5,621,648; 5,880,961; 6,091,999; and 6,407,735. Such techniques, broadly speaking, involve the repeated optical scanning of a part that has been encased in a potting material so that, as successive layers of the part/potting combination are removed, data regarding the dimensions of the part are generated by a computer processing the scanned data of the image of each successive surface remaining after the preceding layer is removed. The optical contrast between the portions of the surface due to the potting material and those due to the material of the part identifies the dimensions of the part itself. Post-acquisition data processing techniques improve the utility of the data for various purposes. One such technique is described in U.S. Pat. No. 6,407,735.

SUMMARY

Commercial embodiments of the techniques and systems disclosed in the patents listed above generally involve what may be called an "X-Axis" approach, meaning that a stage or shuttle carries the part/potting combination linerally back and forth along an axis between separate scanning and material removal stations. This application discloses various embodiments of improved methods and apparatus for cross-sectional scanning of parts, utilizing a so-called "Z-Axis" approach. These embodiments employ a scanning station in which the focal plane of the scanning apparatus never moves in the vertical or Z direction, i.e., the direction in which the stage of the part/potting combination moves. The distinct steps of material removal and scanning alternate with an intermediate step of moving the part/potting combination in the Z direction after a surface layer has been removed, thus placing the newly-created surface back into the focal plane for the next scanning step. To accomplish this, a removal station (not the stage carrying the part/potting combination) repeatedly moves in the +/−X direction, i.e., into and out of the field of view of the scanning station, between scanning steps. The material removal station is specially configured to remove the desired surface layer of the part/potting combination and the created debris, without requiring the separate environment that previously mandated the use of the X-Axis approach in commercial applications.

BRIEF DESCRIPTION OF THE DRAWINGS

The figures illustrate a preferred embodiment and thus it should be understood that minor changes in shape, proportion, size, and the like are not critical to the scope of the disclosure except as specifically noted elsewhere below.

DETAILED DESCRIPTION

In general terms, this application pertains to substantially improved versions of the methods and apparatus for cross-sectional scanning disclosed in U.S. Pat. Nos. 5,139,338; 5,261,648; 5,880,961; and 6,091,099. Each of these documents is incorporated by reference and familiarity with the basic operating principles taught in each of these documents is assumed in the following discussion. Thus, details known in the art will be understood, such as those associated with the removal of successive layers of the part/potting combination, generation of data regarding the dimensions of the part (including the computer processing of the scanned data of the image of each successive surface remaining after the preceding layer is removed), and the post-acquisition data processing techniques that improve the utility of the data for various purposes.

Figure 1:
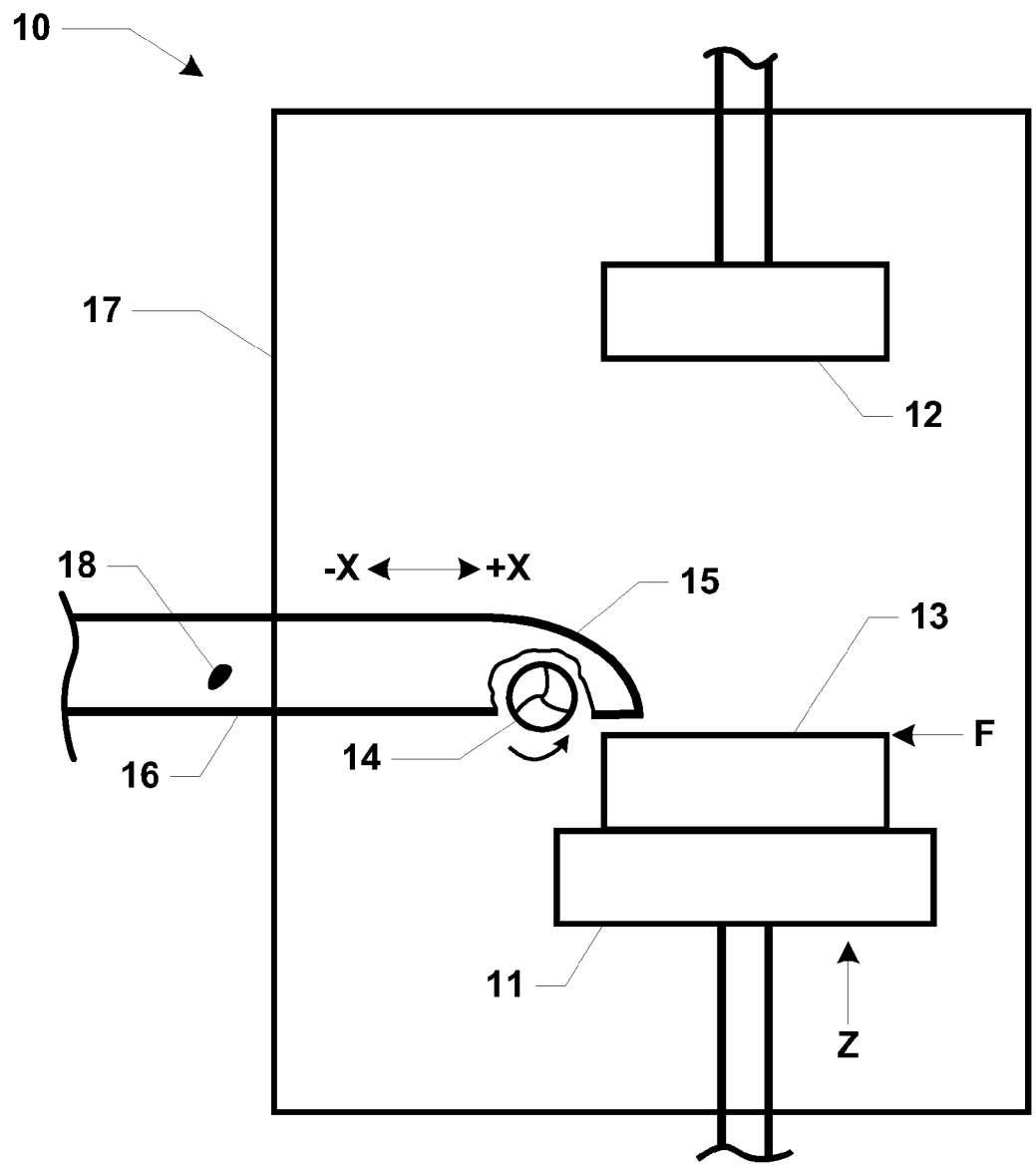
FIG. 1 is a schematic side view of a system according to the detailed description below.
Figure 2:
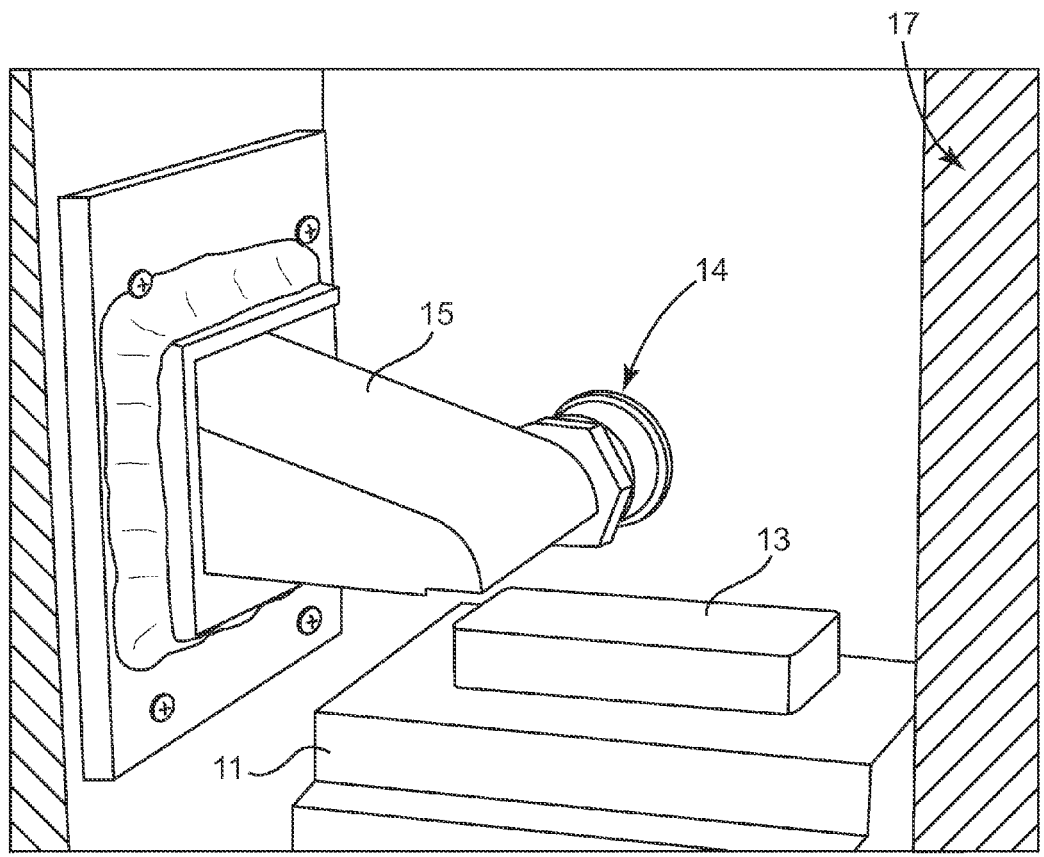
FIG. 2 is a close-up upper perspective view of a prototype embodiment of a portion of FIG. 1.
Figure 3:
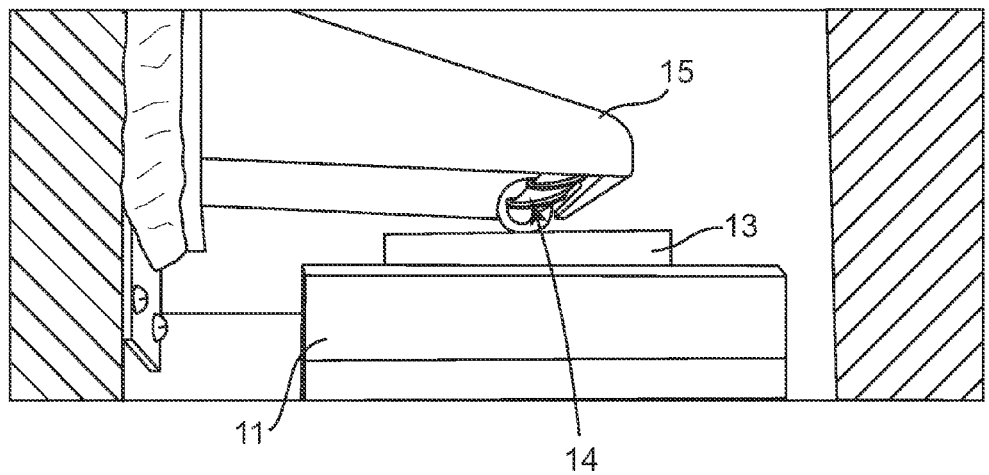
FIG. 3 is a close-up lower perspective view of a portion of FIG. 2.

Referring to FIGS. 1-3, a prototype cross-sectional scanner system 10 comprises vertically moving stage 11 and fixed-focal plane scanner 12. In the preferred embodiment, scanner 12 is stationary with respect to system 10 and thus only the vertical motion of stage 11 need be considered explicitly. However, although it is not preferred, it is possible for scanner 12 to move relative to stage 11, but the remainder of this discussion assumes that only stage 11 moves in the vertical direction with the understanding that the non-preferred approach is also included. Stage 11 supports part/potting combination 13 so that vertical motion of stage 11 advances combination 13 in the vertical direction toward scanner 12. The initial motion places the upper surface of combination 13 at a position corresponding to the height of one thickness of material to be removed above the fixed location F of the focal plane of scanner 12. Then such a thickness is removed from the upper (scanner-facing) surface of combination 13 by cutting subsystem 14 described further below. This places the upper surface so created exactly at the position of the fixed focal plane of scanner 12, and scanning proceeds according to conventional techniques. A repeated series of stepwise motions, each corresponding in distance to the thickness of material to be removed, alternates with removal of such material followed by scanning of the new upper surface created. Thus, each scanning step occurs at the location of the fixed focal plane. The part/potting combination never shuttles in the X or Y directions.

In general, scanner 12 is any multi-pixel scanner, camera, or similar optical image capture device such as a CCD array, line scan camera, or area scan camera. High resolution (155,000 pixels per square centimeter or greater) (megapixel per square inch or greater) image capture equipment is preferred for scanner 12. In this case, a preferred, but not limiting, thickness of each slice is 25.4 micrometers [one thousandth (0.001) inch]. This combination results in data points measured at a scale that is 25.4 micrometers [one thousandth (0.001) inch] in each of the three orthogonal primary directions.

References to thickness measurements should be understood as referring to measurements taken normal to the surface of the part/potting combination 13. The part itself typically is oriented at some non-orthogonal angle within the potting material and thus distances measured in the principal X, Y, and Z planes may expose amounts of the part that are greater than or less than the thickness as measured normal to the surface of the part at the location of measurement.

As shown, part/potting combination 13 is generally rectangular in cross-section in each of the three principal directions. It is preferred, but not required, that combination 13 have maximum dimensions on the order of 44.4 millimeters by 63.5 millimeters by 88.9 millimeters (1¾ inch by 2½ inch by 3½ inch). This is only a preference.

Cutting subsystem 14 is, in general, any means for removing an amount of the upper surface of the part/potting combination. In the embodiment illustrated, it specifically includes a rotating single-end center-cutting end mill supplied by Niagara Cutter of Amherst, N.Y. under their model number A377 as designated by that manufacturer. This device has three flutes in a right-hand orientation at a helix angle of 37° and dimensions (flute diameter by shank diameter by cut length by overall length) of 9.5 millimeters by 9.5 millimeters by 38.1 millimeters by 82.6 millimeters (⅜ inch by ⅜ inch by 1½ inches by 3¼ inches). The device may be uncoated or coated as available from the manufacturer; a preferred coating is TiCN. The use of three flutes is preferred for creation of a smoother surface, but the number of flutes is not by itself a critical parameter. The preferred rotation speed is 1200 rpm. The right-handed orientation, coupled with counter-clockwise rotation (as observed looking at the tip of the device, as illustrated by the curved arrow in FIG. 1) means that the cutting edges advance into the workpiece in the same direction as the advancing hood, i.e., the positive X-direction. It is possible, but not necessary, to continue rotation of the end mill as hood 15 is withdrawn (in the -X direction) so that the rapidly spinning cutting surfaces smooth out the surface of combination 13 to ensure greater accuracy.

The cutting length of cutting subsystem 14 should be greater than the width of part/potting combination 13 to ensure that the entire width of part/potting combination 13 is cut in a single pass. The position of cutting subsystem 14 with respect to the location of part/potting combination 13 is coordinated accordingly.

Hood 15 enables conventional vacuum system 16 to quickly and efficiently remove debris 18 from chamber 17 as such debris is created by cutting subsystem 14 when it removes the layer of part/potting combination 13. The exact shape of hood 15 is not critical. The function of hood 15 is to concentrate the vacuum and keep the debris within a contained volume. In the embodiment illustrated, hood 15 substantially surrounds cutting subsystem 14 but for a relatively small open throat facing the upper surface of the part/potting combination, through which debris will be collected by the vacuum (see especially FIG. 3).

As with the cutting length of cutting subsystem 14, the width of hood 15 (measured in the Y-direction) is greater than the width of part/potting combination 13 to ensure that the entire width is cut in a single pass. Hood 15 is mechanically attached or otherwise coordinated with the position of cutting subsystem 14 so that both advance together (in the X-direction) across the face of part/potting combination 13 to remove the surface layer of material (thus generating the debris).

Any debris 18 generated by such removal is withdrawn through vacuum hood 15, which is attached to conventional vacuum system 16. As illustrated in this embodiment, system 10 further comprises a working chamber 17, which is optional in the sense that system 10 could be incorporated as a subsystem of a larger system if so desired.

Thus, the amount of motion required of the various components of system 10 is substantially reduced compared to prior commercial embodiments. To summarize, focal plane F remains fixed at all times; table 11 (and thus part/potting combination 13) moves only in the Z direction and not at all in the X or Y directions; hood/vacuum system 15, 16 moves only in the +/-X directions and not in the Y or Z directions; and cutting subsystem 14 (in the preferred embodiment illustrated) comprises a rotating end mill, having an axis of symmetry located such that it is coordinated with the Z position of the part/potting combination 13 to thereby remove only the necessary and desired amount of material as that axis moves in only the +/-X direction and not the Y or Z directions. The substantial reduction in the amount of moving subassemblies enables a substantial reduction in the overall size of the system 10, because it reduces overall structural, mechanical, and electrical supporting equipment. This makes the system 10 highly suitable for use with small part/potting combinations 13 such as those having the non-limiting dimensions given above.

The techniques described above may be contrasted to the disclosure of the patents listed above, which specifically disclose the use of separate, dedicated locations for the material removal station and the scanning station, such stations being separated from each other along the so-called X axis. The time required to shuttle the stage bearing the part/potting combination back and forth between these physically separate stations reduces the cycle time of the entire process compared to the approach disclosed above. By contrast, very low cycle times of approximately 8-10 seconds are believed possible in commercial production of the approach described above.

It is well known to use computers to control the operation and location of the system as well as to process the data generated by the scanning subsystem. The preferred, but not required, technique to convert the scanning data is disclosed in the patents incorporated by reference above, as well as U.S. Pat. No. 6,407,735, which is also incorporated by reference.

Application to Cross-Sectional Scanning Systems

The techniques described above may be employed in a cross-sectional scanning system of the following general design. Details of particular embodiments of such systems are in the patents incorporated by reference above.

The system produces electronic data representations of an object or part. The major components of the system are: (1) a data gathering station having a focal plane, the position of the focal plane being fixed relative to the surface of the part; (2) a material removal station that moves into and out of position over the surface of the part; and (3) a table providing only vertical relative movement of the part to put the surface at the position of the focal plane. The data gathering station typically, but not necessarily, comprises: (1) an image data acquisition device for successively acquiring images of the part after removal of a predetermined contour; and (2) an electronic device operatively associated with the image data acquisition device for receiving and storing the images. The material removal station typically, but not necessarily, comprises: (1) a tool constructed and arranged to remove a predetermined contour of material from the part; and (2) a drive mechanism constructed and arranged to provide relative movement between the tool and the part. The table holds the part and is moved by a drive mechanism constructed and arranged to provide only vertical relative movement of the table; and a means to determine the relative locations of the part and the focal plane along the vertical direction.

The operation of a typical configuration of such a system is as follows. The image data acquisition device successively acquires images of the part after removal of a predetermined contour. The tool is moved into and out of relative material removing engagement with the part. The relative movement between the table and the tool along the path is such that the part and the tool are moved in material removal alignment for removing a predetermined contour of material from the part and in imaging alignment to the image data acquisition device after removal of a predetermined contour. The position determining apparatus actuates the image data acquisition device at predetermined positions of the part relative to the tool. For example, a linear encoder with a scale, a sensor, and a computer may be arranged to send signals to the computer in response to the relative movement between the sensor and the scale. The computer is programmed to determine the position of the scale relative to the sensor in response to the signals received from the sensor. Thus, because the scale and sensor are operatively associated with each other, the position of the part relative to the tool along the path is incrementally determined by the computer.

Commercial embodiments of such systems employ visible light (400-700 nm wavelength) for illumination and scanners sensitive to light typically having a wavelength centered on 550 nm. However, such values are not critical provided that sufficient contrast is provided at the detection wavelength chosen. Similarly, while directly impinging illumination and scanning normal to the surface have been illustrated, as is commercially common, more complicated geometries are possible but not preferred.

While the above description refers to many specific details for the sake of explanation, these details should not be construed as limitations unless explicitly included in the following claims.

We claim:

1. A system for scanning a part having an outer surface, the system comprising:
    a data gathering station;
    a material removal station including a vacuum, a hood, and a cutting tool that rotates about a Y-axis; and
    a table providing only vertical, Z-axis movement of the part relative to the data gathering station along a vertical path,
    wherein the part is encased in a potting material to form an assembly, wherein the material removal station is configured to move horizontally in an X-axis perpendicular to the Y-axis proximate the assembly to remove a thin and consistent portion of the assembly to expose a surface and the vacuum is arranged and configured to collect the removed portion of the assembly, and wherein the cutting tool has a cutting length in the Y-direction greater than an assembly width in the Y-direction.

2. The system of claim 1, in which the data gathering station comprises at least one of: an image data acquisition device for successively acquiring images of the part after removal of a predetermined contour; and an electronic device operatively associated with the image data acquisition device for receiving and storing the images.

3. The system of claim 1, in which the material removal station further comprises a drive mechanism constructed and arranged to provide relative horizontal movement between the tool and the part.

4. The system of claim 1, in which the table holds the part and further comprises a drive mechanism constructed and arranged to provide vertical movement between the table and the data gathering station along the vertical path.

5. The system of claim 1, wherein the cutting tool includes at least one blade configured to rotate on a rotary surface, the rotary surface making tangential contact with the assembly such that a direction of travel at the point of tangential contact is opposite a direction of travel of the material removal station.

6. A method for producing electronic data representations of an object having a plurality of surfaces, the method comprising:
    encasing the object within a preselected encasing material to form an encasement, such encasing being done so that all surfaces of the object are coated with the encasing material and so that the encasing material substantially fills all interior volumes of the object;
    removing successively from the encasement, by a cutting tool that rotates about a Y-axis, a plurality of thin and consistent layers of material, each layer of material removed having predetermined dimensions of length, width and depth and a predetermined geometric shape, so as to expose an encasement surface, and assigning a value to each layer representative of its elevation within the object, the cutting tool having a cutting length in the Y-direction greater than an encasement width in the Y-direction;
    vacuuming debris created from removing the plurality of layers by horizontal X-axis movement of a vacuum proximate the encasement surface;
    acquiring an electronic representation of selected exposed encasement surfaces after each layer has been removed and the debris is vacuumed; and
    processing each electronic representation to create a predetermined electronic representation of each the encasement surface.

7. The method of claim 6, in which the selected electronic representation is a solid model of the object and in which the processing step includes converting each electronic representation into a layered point cloud representative of the object.

8. The method of claim 7, in which the method further comprises lofting a surface onto each layered point cloud.

9. The method of claim 6, in which the method further comprises importing each layer into CAD space and stacking the layers according to their assigned elevation value.

10. The method of claim 6, and further including creating a solid between adjacent layers.

11. The method of claim 6, in which the selected electronic representation is a solid model of the object.

12. The method of claim 6, in which the selected electronic representation is a surface model of the object.

13. The method of claim 6, in which the layer removing step removes contour of material such that successively exposed surfaces of the object are substantially parallel to each other, the method further including: identifying a feature of interest in the object; and orienting the object such that the exposed surfaces of the object are non-parallel to the feature of interest so that at least one exposed surface extends through the feature of interest.

14. The method of claim 6, in which the selected electronic representation is a surface model of the object and in which the processing step includes convening each electronic representation into a line art drawing defining the perimeter edges of the internal and external edges of the object.

15. The method of claim 14, in which the processing step further includes stacking the line art drawings and lofting a surface thereon.

16. The method of claim 14, in which the processing step further includes converting the line art drawings into a vector data file.

17. The method of claim 16, in which the processing step further includes importing the vector data file into 3D CAD space and lofting a surface thereon.

18. The method of claim 6, in which the layers have upper and lower surfaces and a substantially uniform thickness, the upper and lower surfaces being substantially parallel to each other.

19. The method of claim 6, in which the electronic representation is a raster planar image and in which the processing step further includes importing the raster planar image into 3D CAD space and converting the imported images into a solid model of the object.

20. The method of claim 6, in which the layers have upper and lower surfaces being substantially parallel to each other and in which the layers increase in thickness as successive layers of the encasement are removed to form each the predetermined contour.

21. The method of claim 6, in which the layers have upper and lower surfaces being substantially parallel to each other and in which the layers decrease in thickness as successive layers of the encasement are removed to form each the predetermined contour.

22. The method of claim 6, in which the predetermined contour has a substantially uniform thickness of about one thousandth of one inch.

23. The method of claim 6, wherein the cutting tool includes at least one blade configured to rotate on a rotary surface, the rotary surface making tangential contact with the encasement such that a direction of travel at the point of tangential contact is opposite a direction of travel of the vacuum.

24. An apparatus for producing electronic data representations of an object, the object being formed from at least one material, the apparatus comprising:
 a material removal station having a mill having a cutting tool that rotates about a Y-axis, a vacuum, and a hood, the material removal station for removing a thin and consistent predetermined layer of material from the object, the cutting tool having a cutting length in the Y-direction greater than an object width in the Y-direction;
 a data gathering station having an image data acquisition device for successively imaging the object after removal of a predetermined layer, the image data acquisition device having a fixed position focal plane;
 a stage movable in only a vertical direction along a vertical Z-axis perpendicular to the fixed position focal plane; and
 a device for storing data gathered by the image data acquisition device, wherein
 the stage comprises:
 a table for holding the object, wherein the table is moved only in a single direction to maintain the object in imaging alignment with the image data acquisition device before and after the mill moves into and out of position proximate the object for removing the predetermined layer of material, and
 wherein the material removal station moves in an X-axis direction substantially perpendicular to the Z-axis into and out of relative material removing position in which the material removal station removes and collects the predetermined layer of material.

25. The apparatus of claim 24, in which the data gathering station is capable of producing a three-dimensional drawing of the object.

26. The apparatus of claim 24, in which the object is encased within an encasing material to form an encasement and in which the mill removes a predetermined layer of the encasement.

27. The apparatus of claim 24, in which the mill comprises an end mill including at least one flute, the end mill being rotated about an axis substantially perpendicular to the axis of motion of the stage and substantially parallel to the common plane, such that a planar surface of the object is exposed by the removal of material by at least one flute as the end mill is rotated.

28. The apparatus of claim 24, in which the removal of the predetermined layer of material exposes an object surface and an encasing material surface and in which the object surface contrasts with the encasing material surface so that a line of demarcation may be determined between the surfaces.

29. The apparatus of claim 24, in which the predetermined layer of material is of substantially uniform thickness.

30. The apparatus of claim 24, wherein the cutting tool includes at least one blade configured to rotate on a rotary surface, the rotary surface making tangential contact with the object such that a direction of travel at the point of tangential contact is opposite a direction of travel of the material removal station.

31. A method of scanning a part, comprising:
 encasing the part into a potting material to form an assembly;
 while the assembly is not moving, progressively horizontally removing, by a cutting tool that rotates about a Y-axis, a thin and consistent portion of the assembly to expose a surface, the cutting tool having a cutting length in the Y-direction greater than an assembly width in the Y-direction;
 vacuuming the removed portion away from the assembly by horizontal X-axis movement perpendicular to the Y-axis of a vacuum proximate the surface;
 moving the surface substantially only vertically along a Z-axis to a position in a fixed position focal plane; and
 scanning the surface.

32. The method of claim 31, further comprising repeating progressively horizontally removing, by a cutting tool that rotates about a Y-axis, a portion of the assembly to expose a surface and moving the surface substantially only vertically along a Z-axis to a position in a fixed position focal plane after scanning the surface.

33. The method of claim 31, wherein the cutting tool includes at least one blade configured to rotate on a rotary surface, the rotary surface making tangential contact with the assembly such that a direction of travel at the point of tangential contact is opposite a direction of travel of the vacuum.

34. A system for scanning an object, wherein the object is encased in potting material to form a potting assembly prior to scanning, the system comprising:
 a data gathering station including an image data acquisition device that gathers data from a focal plane;
 a material removal station including a rotating end mill that rotates about a Y-axis, a vacuum and a hood, the end mill having a cutting length in the Y-direction greater than a potting assembly width in the Y-direction; and
 a stage on which the potting assembly is secured,
 wherein the stage moves toward the data gathering station on a fixed line transverse to the focal plane,
 wherein the system provides for selectively changing a distance between the object, when the object is encased in a potting assembly and secured to the stage, and the data gathering station along the fixed line,
 wherein the material removal station repeatedly removes a series of thin and consistent pre-determined portions of the potting assembly to expose a new surface on the potting assembly that is positioned in the focal plane as the stage moves toward the data gathering station when the object is encased in the potting assembly and secured to the stage, and wherein the stage moves only along a Z-axis, the image data acquisition device is stationary and the material removal station moves proximate and distal the potting assembly only along an X-axis perpendicular to the Z-axis.

35. The system of claim 34, wherein the image data acquisition device successively acquires images of the potting assembly after removal of the predetermined portions, in which the data gathering station further includes an electronic device operatively associated with the image data acquisition device for receiving and storing the images.

36. The system of claim 34, in which the material removal station further includes a drive mechanism constructed and arranged to provide relative movement between the tool and the potting assembly.

37. The system of claim 34, wherein the fixed line is vertical and the stage further includes a drive mechanism constructed and arranged to provide vertical movement between the stage and the data gathering station along the vertical fixed line.

38. The system of claim 34, wherein the rotating end mill includes at least one blade configured to rotate on a rotary surface, the rotary surface making tangential contact with the potting assembly such that a direction of travel at the point of tangential contact is opposite a direction of travel of the material removal station.

39. An apparatus for producing electronic data representations of an object, the object being formed from at least one material, the apparatus comprising:
 a material removal station;
 a data gathering station having a fixed position focal plane; and
 a stage movable in only a Z direction along a Z-axis, perpendicular to the fixed position focal plane;
 wherein the material removal station includes:
  a vacuum and a hood, and a tool for removing a predetermined layer of material from the object, the tool configured to rotate about a Y-axis, the tool having a cutting length in the Y-direction greater than an object width in the Y-direction;
 wherein the data gathering station includes: an image data acquisition device for successively imaging the object after removal of a predetermined layer; and data storage device for storing gathered by the image data acquisition device for imaging; and wherein the stage includes:
  a table for holding the object; wherein the table moves only in a single direction to maintain the object in imaging alignment with the image data acquisition device for successively imaging the object before and after the tool is moved into and out of position for removing a layer of material; and
 wherein the material removal station moves only substantially perpendicular to the Z-axis in an X-axis into and out of relative material removing position proximate the object in which the material removal station removes and collects a thin and consistent predetermined layer of material.

40. The apparatus of claim 39, in which the data gathering station further includes means for manipulating data gathered by the image data acquisition device and stored in the data storage device to produce a three-dimensional drawing of the object.

41. The apparatus of claim 39, in which the object is encased within an encasing material to form an encasement and in which the tool removes a predetermined layer of the encasement.

42. The apparatus of claim 39, in which the material removal station further includes an end mill including at least one tool, the end mill being rotated about an axis substantially perpendicular to the axis of motion of the stage such that a planar surface of the object is exposed by the removal of material by at least one tool as the end mill is rotated.

43. The apparatus of claim 39, in which the removal of the predetermined layer exposes an object surface and an encasing material surface and in which the object surface contrasts with the encasing material surface so that a line of demarcation may be determined between the surfaces.

44. The apparatus of claim 39, in which the predetermined layer is of substantially uniform thickness.

45. The apparatus of claim 39, in which the data gathering station further includes means for manipulating data gathered by the imaging and stored in the data storage device to produce a three-dimensional drawing of the object.

46. A method of scanning an object, the method comprising:
 (a) encasing the object into a potting material to form a potting assembly;
 (b) while the potting assembly is not moving, progressively removing, with a material removal station including a cutting tool that rotates about a Y-axis, a thin and consistent portion of the potting assembly to expose a surface, the cutting tool having a cutting length in the Y-direction greater than an object width in the Y-direction;
 (c) vacuuming the removed portions of the potting assembly by X-axis movement perpendicular to the Y-axis of the material removal station;
 (d) moving the potting assembly with a stage substantially only vertically along a Z-axis to a position in a fixed position focal plane; and
 (e) scanning the surface with an image data acquisition device,
 wherein the stage moves only along a Z-axis, the image data acquisition device is stationary, and the material removal station moves proximate and distal the potting assembly only along an X-axis perpendicular to the Z-axis.

47. The method of claim 46, further comprising repeating (b) and (c) after (d) after (e).

48. A method of producing electronic data representations of an object, the object having a plurality of surfaces, wherein the method comprises:
 providing a system for scanning the object, wherein the object is encased in potting material to form a potting assembly prior to scanning, the system comprising:
  a data gathering station including an image data acquisition device that gathers data from a focal plane, a material removal station including a cutting tool that rotates about a Y-axis, the cutting tool having a cutting length in the Y-direction greater than a potting assembly width in the Y-direction, and a stage on which the potting assembly is secured;
  wherein the stage moves toward the data gathering station in a Z-axis on a fixed line transverse to the focal plane;
  wherein the system provides for selectively changing a distance between the object, when the object is encased in a potting assembly and secured to the stage, and the data gathering station along the fixed line;
  wherein the material removal station repeatedly removes a series of thin and consistent pre-determined portions of the potting assembly to expose a new surface on the potting assembly that is positioned in the focal plane as the stage moves toward the data gathering station when the object is encased in the potting assembly and secured to the stage;

encasing the object within a preselected encasing material to form a potting assembly, such encasing being done so that all of the plurality of surfaces of the object are coated with the encasing material and so that the encasing material substantially fills all interior volumes of the object;

removing successively from the encasement, by the cutting tool, a plurality of layers of material, each layer of material removed having predetermined dimensions of length, width and depth and a predetermined geometric shape, so as to expose an encasement surface, and assigning a value to each layer representative of its elevation within the object;

vacuuming the removed layers of material by horizontal X-axis movement perpendicular to the Y-axis of a vacuum proximate the encasement surface;

acquiring an electronic representation of selected exposed encasement surfaces after a predetermined layer has been removed; and processing each electronic representation to create a predetermined electronic representation of each encasement surface.

49. The method of claim 48, wherein the selected electronic representation is a three dimensional point cloud representative of the object.

50. The method of claim 48, in which the selected electronic representation selected from the group consisting of a solid model of the object and a surface model of the object.

51. The method of claim 48, wherein the acquiring step includes scanning each encasement surface using a scanner to create a scanned image of each encasement surface.

52. The method of claim 48,
wherein the removing step includes removing a contour of material such that successively exposed encasement surfaces of the object are substantially parallel to each other, the method further comprising:
identifying a feature of interest in the object; and
orienting the object such that the exposed encasement surfaces of the object are non-parallel to the feature of interest so that at least one exposed encasement surface extends through the feature of interest.

53. The method of claim 48, wherein the layers have upper and lower encasement surfaces and a substantially uniform thickness, the upper and lower surfaces being substantially parallel to each other.

* * * * *